(12) United States Patent
Fox

(10) Patent No.: US 8,647,626 B2
(45) Date of Patent: *Feb. 11, 2014

(54) COMPOSITIONS COMPRISING TNF-SPECIFIC ANTIBODIES FOR ORAL DELIVERY

(71) Applicant: Avaxia Biologics, Incorporated, Lexington, MA (US)

(72) Inventor: Barbara S. Fox, Wayland, MA (US)

(73) Assignee: Avaxia Biologics, Incorporated, Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/912,569

(22) Filed: Jun. 7, 2013

(65) Prior Publication Data

US 2013/0337018 A1 Dec. 19, 2013

Related U.S. Application Data

(60) Continuation of application No. 13/860,029, filed on Apr. 10, 2013, and a division of application No. 13/452,026, filed on Apr. 20, 2012, now Pat. No. 8,435,526, and a division of application No. 12/753,438, filed on Apr. 2, 2010, now Pat. No. 8,182,818, and a continuation of application No. PCT/US2008/078543, filed on Oct. 2, 2008.

(60) Provisional application No. 61/055,215, filed on May 22, 2008, provisional application No. 61/015,507, filed on Dec. 20, 2007, provisional application No. 60/976,876, filed on Oct. 2, 2007.

(51) Int. Cl.
*A61K 39/395* (2006.01)

(52) U.S. Cl.
USPC .................. 424/158.1; 424/130.1; 424/157.1

(58) Field of Classification Search
None
See application file for complete search history.

(56) References Cited

PUBLICATIONS

Shojaei A H, "Buccal Mucosa as a route for systemic drug delivery: a review", Journal of Pharmacy and Pharmaceutical Sciences, 1(1):15-30, 1998.

*Primary Examiner* — Robert Landsman
(74) *Attorney, Agent, or Firm* — Elmore Patent Law Group, P.C.; Darlene A. Vanstone; Carolyn S. Elmore

(57) ABSTRACT

In accordance with the invention, the development and use of antibodies within the digestive tract is provided. Antibodies are described that are used to treat disorders associated with altered permeability of the digestive tract. Antibodies are described with increased stability within the environment of the digestive tract. Antibodies are described with enhanced permeability to a compromised digestive tract.

6 Claims, No Drawings

```
                        SEQUENCE LISTING

<160> NUMBER OF SEQ ID NOS: 3

<210> SEQ ID NO 1
<211> LENGTH: 19
<212> TYPE: PRT
<213> ORGANISM: Bovine

<400> SEQUENCE: 1

Asp Pro Arg Cys Lys Thr Thr Cys Asp Cys Pro Pro Pro Glu Leu
1               5                   10                  15

Pro Gly Gly

<210> SEQ ID NO 2
<211> LENGTH: 20
<212> TYPE: PRT
<213> ORGANISM: Bovine

<400> SEQUENCE: 2

Asp Pro Thr Cys Lys Pro Ser Pro Cys Asp Cys Pro Pro Pro Glu
1               5                   10                  15

Leu Pro Gly Gly
            20

<210> SEQ ID NO 3
<211> LENGTH: 19
<212> TYPE: PRT
<213> ORGANISM: Bovine

<400> SEQUENCE: 3

Asp Pro Arg Cys Lys Arg Pro Cys Asp Cys Pro Pro Pro Glu Leu
1               5                   10                  15

Pro Gly Gly
```

COMPOSITIONS COMPRISING TNF-SPECIFIC ANTIBODIES FOR ORAL DELIVERY

RELATED APPLICATIONS

This application is a continuation application of U.S. application Ser. No. 13/860,029, filed on Apr. 10, 2013, which is a divisional application of U.S. application Ser. No. 13/452,026, filed Apr. 20, 2012, now U.S. Pat. No. 8,435,526, issued May 7, 2013, which is a divisional application of U.S. application Ser. No. 12/753,438, filed Apr. 2, 2010, now U.S. Pat. No. 8,182,818, issued May 22, 2012, which is a continuation of International Application No. PCT/US2008/078543, which designated the United States and was filed on Oct. 2, 2008, published in English, which claims the benefit of U.S. Provisional Application Nos. 60/976,876 filed on Oct. 2, 2007; 61/015,507 filed on Dec. 20, 2007; and 61/055,215 filed on May 22, 2008. The entire teachings of the above applications are incorporated herein by reference.

FIELD OF THE INVENTION

This invention describes the development and use of antibodies within the digestive tract.

BACKGROUND OF THE INVENTION

Diseases and disorders of the digestive tract cause significant morbidity and mortality and there is a need for new therapeutics and therapeutic strategies. Diseases of the digestive tract include mucositis, aphthous stomatitis, esophagitis, inflammatory bowel disease, irritable bowel syndrome, celiac disease, trauma to the digestive tract, infections of the digestive tract and cancers of the digestive tract.

For some digestive tract diseases, there are no effective treatments available. One example of such an unmet medical need is mucositis, a serious and painful condition that results from radiation therapy and/or chemotherapy for cancer treatment. According to a recent report by the National Comprehensive Cancer Network, mucositis is the most significant adverse symptom of cancer therapy reported by patients {Bensinger et al., 2008, J Natl Compr Canc Netw, 6 Suppl 1, S1-21 quiz S22-4}. Damage can occur throughout the digestive tract and frequently results in cessation or dose reduction of the cancer therapy {Blijlevens and Sonis, 2007, Ann Oncol, 18, 817-26}. Oral mucositis presents with pain, erythema and deep, diffuse ulcers that can cause difficulty speaking, eating and swallowing and significantly impair daily functioning. Opioid analgesia, IV hydration, use of a liquid diet and total parenteral nutrition may be used in patients suffering from oral mucositis. Intestinal mucositis presents with nausea, vomiting, abdominal pain and diarrhea, sometimes with blood loss. It most commonly affects the small intestine, but is also seen in the stomach and large intestine. There is a single medication approved for the treatment of mucositis, palifermin {Blijlevens and Sonis, 2007, Ann Oncol, 18, 817-26}, but it is only used in a limited subset of patients. Therefore, there is a need for additional therapeutics for mucositis.

Another example of an unmet medical need is recurrent aphthous stomatitis (RAS), a common oral disease, affecting 5-20% of the normal population {Porter et al., 1998, Crit. Rev Oral Biol Med, 9, 306-21}. RAS presents with recurrent bouts of rounded, shallow painful ulcers on the mucosa of the mouth. The most common form is minor RAS, where the ulcers are usually less than 5 mm in diameter. The ulcers usually occur on the labial and buccal mucosa and the floor of the mouth and are uncommon on the gingival, palate or dorsum of the tongue. The lesions heal within 10-14 days. Major RAS is less common, with larger ulcers that persist for up to 6 weeks and often heal with scarring. The etiology of RAS is unknown, and there are no approved pharmacotherapies.

For some diseases of the digestive tract, treatments are already available. For example, both small molecule and biological therapies are available for the treatment of Crohn's disease and ulcerative colitis, the two forms of inflammatory bowel disease {Kozuch and Hanauer, 2008, World J Gastroenterol, 14, 354-77}. However, all of these medications have limitations, either in efficacy or in safety, and there is a need for new therapeutic approaches and strategies.

Antibodies are an important class of pharmaceuticals. Specific antibody therapeutics have been shown to be highly effective in treating cancers and autoimmune disease, and their use has been of great benefit to afflicted patients. Antibodies are generally highly specific for a particular target and thus tend to have less off-target toxicity than is seen with small molecule therapeutics.

It would be advantageous to be able to apply antibody therapeutics to diseases of the digestive tract. Most antibody therapies in current use are designed to be delivered systemically and are administered to patients by injection. Injected antibodies have been shown to be useful in the treatment of inflammatory bowel disease, and may also be useful in the treatment of other diseases of the digestive tract. However, administration of antibodies systemically may affect physiological processes throughout the body, rather than just within the digestive tract, and this may be disadvantageous for some diseases. For instance, anti-TNF antibodies used for the treatment of inflammatory bowel disease are associated with serious side effects {Lin et al., 2008, Clin Immunol, 126, 13-30}. Therefore, it would be useful to be able to apply antibody therapeutics directly to the digestive tract.

There have been two obstacles to the use of antibody therapeutics within the digestive tract. First, the digestive tract is a hostile environment for protein therapeutics, with low pH environments designed to denature ingested proteins and proteases designed to digest ingested proteins. The oral cavity contains proteases derived from the host and from resident microorganisms. Polymorphonuclear leukocytes are secreted in the crevicular fluid, and some of these cells lyse before they are swallowed, releasing lysozyme into the fluid of the oral cavity. Bacteria present as part of the normal oral flora express proteases capable of degrading immunoglobulin. These proteases include IgA1 protease, IdeS, argingipain and SpeB. The stomach is highly acidic, and contains the protease pepsin, which is active at low pH. The small intestine contains additional proteases, including trypsin and chymotrypsin. The bacteria of the large intestine further express varied proteases that degrade ingested protein. Therefore, there is a need to develop approaches to deliver antibody therapeutics to the digestive tract where the antibody will not be degraded. This invention describes methods and compositions for antibodies that have improved stability within the oral cavity and the gastrointestinal tract.

Second, many of the targets that would be useful for antibody therapeutics have not been thought to be accessible to antibody applied to the luminal surface of the digestive tract. One of the functions of the digestive tract is to create a barrier to prevent the entry into the systemic circulation of a variety of foreign agents that enter the digestive tract, including food and microorganisms. Under normal circumstances, this barrier would exclude topically applied antibody from accessing targets expressed on the basolateral face of the epithelial cells lining the digestive tract, or on the mucosa or submucosa. Therefore, there is a need to develop approaches to targeting antibodies to these targets that lie below the normal barrier of the digestive tract. This invention describes the use of antibodies to treat patients with altered permeability barriers in the digestive tract, allowing topically applied antibody to access the appropriate targets.

SUMMARY OF THE INVENTION

This invention describes the development and use of antibodies within the digestive tract. Antibodies are described that are used to treat disorders associated with altered permeability of the digestive tract. Antibodies are described with increased stability within the environment of the digestive tract. Antibodies are described with enhanced permeability to a compromised digestive tract.

Definitions

For the purposes of the invention, the digestive tract consists of the mouth, pharynx, esophagus, stomach, small intestine (duodenum, jejunum, ileum), large intestine (cecum, colon, rectum) and anus.

For the purposes of the invention, the "oral cavity" is understood to include the mouth, the pharynx and the esophagus. The term "oral degradation" of an antibody is used herein to mean degradation of an antibody in the oral cavity by endogenous or exogenous enzymes present in the oral cavity.

For the purposes of the invention, the "gastrointestinal tract", or "GI tract" is understood to include the stomach, small intestine (duodenum, jejunum, ileum), large intestine (cecum, colon, rectum) and anus. The term "gastric digestion" as used herein is understood to describe digestion in the stomach, small intestine and large intestine. The term "gastric degradation" of an antibody is used herein to refer to degradation of an antibody in the stomach, small intestine, large intestine by endogenous or exogenous enzymes present in the stomach, small intestine and large intestine or due to exposure to acidic conditions during gastric digestion.

The terms "antibody" and "antibodies" are used herein to refer to compositions or preparations comprising one or more antibodies. The use of the singular terms "a" or "an" or "the" antibody are not meant to be limited to a single antibody when it is clear that more than one antibody is present in the composition or preparation. In addition, unless indicated otherwise, the singular term for "antibody" may include a collection of antibodies that are not necessarily heterogenous in their structures or specificities.

The term "stabilized antibody" as used herein is understood to describe an antibody or antibody preparation that has been processed to make it more stable to degradation in the digestive tract when administered topically. A stabilized antibody excludes the addition of J chain proteins, secretory component, or other similar proteins that are used by the secretory immune system to stabilize secreted antibody, whether those additional proteins are natural or synthetic. As compared to an antibody that has not been processed in accordance with the invention, a stabilized antibody that is processed in accordance with the invention is degraded more slowly or to a lesser extent by endogenous enzymes present in the oral cavity or by exogenous enzymes derived from microorganisms resident in the oral cavity as compared to antibodies and antibody preparations that have not been treated or processed in accordance with the invention. Alternatively or in addition, as compared to an antibody that has not been processed in accordance with the invention, a stabilized antibody that is processed in accordance with the invention is degraded more slowly or to a lesser extent by gastric digestion which includes digestion by endogenous or exogenous enzymes present in the stomach, small intestine and large intestine and/or by the acidic conditions present in the stomach. "Stabilized antibodies" are also referred to as "antibodies with enhanced stability to degradation in the oral cavity and/or the GI tract".

The term antibody with enhanced mucosal permeability as used herein is understood to describe an antibody that has been processed to make it more permeable to a compromised mucosal barrier, as compared to an antibody that has not been processed in accordance with the invention.

The term "targets below the mucosal barrier" is defined as targets located on the basal side of the epithelium, targets expressed in the submucosa, targets expressed in the lateral intercellular space, targets expressed in the lamina propria, targets expressed in the central nervous system, and targets expressed in the systemic circulation.

The term "topical application" to the GI tract is defined as local and/or surface administration to the oral cavity, delivery by oral or rectal administration to the GI tract, or administration by any other route that brings the antibody in contact with the luminal aspect of the GI tract.

The term "apical receptors" refers to endogenous transmembrane proteins expressed in the cell membrane of cells facing the luminal side of the intestinal tract.

The term "TNF" as used herein is used to describe the cytokine TNF-a.

The term "autoimmune disease that targets the GI tract" is used to describe those autoimmune diseases that are known to involve substantial damage to the GI tract and consist of ulcerative colitis and Crohn's disease (together known as inflammatory bowel disease), type I diabetes mellitus and systemic lupus erythematosus (SLE). This definition excludes celiac disease.

The term "glycoform" is used herein to describe an antibody with a defined pattern of glycosylation. The pattern of glycosylation includes both the location and structure of attached carbohydrate. A glycoform may be defined by determination of the molecular structure. Alternatively, a glycoform may be defined by a pattern of lectin binding.

The term "carbohydrate" in this application is used interchangeably with the terms "glycan" or "oligosaccharide".

As used herein the term "compromised" as it relates to the GI tract and the mucosal barrier of the GI tract is understood to mean that one or more areas of the GI tract is permeable such that an antibody applied to such permeable area of the GI tract is capable of crossing the mucosal membrane of the permeable area of the GI tract while remaining intact.

DETAILED DESCRIPTION OF THE INVENTION

This invention relates to the application of antibodies and stabilized antibodies to the gastrointestinal tract of a patient including a patient with altered permeability of the digestive tract.

This invention describes the use of topical antibody therapeutics for use in patients with barrier defects of the digestive tract. In these patients, topically applied antibody is able to cross the mucosal barrier and access targets below the mucosal barrier.

This invention also describes the development and use of antibodies with increased stability in the digestive tract, also referred to herein as stabilized antibodies. Such antibodies of the invention may be used in patients with barrier defects of the digestive tract or in patients without barrier defects of the digestive tract.

Stabilized Antibodies

Topical administration of antibody to the digestive tract is challenging because the digestive tract degrades and digests the topically applied antibodies. Enzymes in the oral cavity, primarily derived from commensal and pathogenic bacteria living within the oral cavity, degrade antibody in the oral cavity. In the stomach, the low pH and the protease pepsin degrade ingested immunoglobulin. In the small intestine, the enzymes trypsin and chymotrypsin, among others, degrade ingested antibody. In the large intestine, bacterially-derived proteases degrade ingested antibody. Antibodies with improved stability in the oral cavity would be preferred for topical application to the oral cavity. Antibodies with improved stability to gastric digestion would be preferred for topical application to the GI tract.

Immunoglobulins contain substantial amounts of carbohydrate. The hinge region of IgG, IgA and IgD can contain both N- and O-linked carbohydrate, while other regions of the heavy chain contain primarily N-linked carbohydrates. There is significant heterogeneity in immunoglobulin glycosylation. For example, human IgG has a principal N-linked glycosylation site at Asn-297. There are 32 different carbohydrates that may be present at the Asn-297 site: 16% of sites are comprised of a bi-antennary carbohydrates with both arms terminating in galactose; in 35% of sites, a terminal galactose is missing from one of the arms, exposing a GlcNAc residue; in 35% of sites, the terminal galactose is missing from both of the arms; the remaining 14% of sites contain sialylated variants. Additional diversity arises from the presence or absence of bisecting GlNAc residues and core fucose. Similar complexity and diversity is seen with other isotypes and in other species.

Carbohydrates on immunoglobulin serve many functions. They participate in binding to Fc receptors, facilitate cellular transport, secretion and clearance, bind to pathogens, maintain solubility and conformation, and participate in binding events to lectins such as mannan-binding lectin. In addition, carbohydrate plays a role in protecting immunoglobulin from proteolytic degradation.

The hinge region is the site on the immunoglobulin molecule that is most sensitive to proteolysis. Human IgA1 contains a 23 amino acid hinge region with 9 potential glycosylation sites, of which five (Thr-228, Ser-230, Ser-232, Thr-225, and Thr-236) are fully or partially occupied; a sixth sugar is present at Ser-224, Thr-233 or Ser-240 on 5-10% of IgA1 molecules. Bovine IgG1 has an extended hinge region that resembles the hinge region of human and mouse IgA1. Bovine IgG1 also contains Ser and Thr residues in the hinge region and appears to contain O-linked carbohydrates, based on binding of the lectin jacalin {Porto et al., 2007, J Dairy Sci, 90, 955-62}. Therefore, some of the stability of bovine immunoglobulin to proteolytic digestion appears to be due to O-linked glycosylation at the hinge region. Some mouse IgG2b molecules are O-glycosylated at Thr-221A in the hinge region, predominantly with a tetrasaccharide composed of Gal-NAc, galactose, and two N-glycosylneuraminic acid residues. The carbohydrate addition covers the portion of the hinge region that is cleaved by papain and results in increased resistance to papain digestion {Kim et al., 1994, J Biol Chem, 269, 12345-50}.

Glycosylation outside of the hinge region is primarily N-linked glycosylation. Glycosylation of immunoglobulin outside of the hinge region can also affect the sensitivity to proteolysis. U.S. Pat. No. 6,720,165 discloses methods whereby the sensitivity of immunoglobulin molecules to proteolysis is increased by removal of carbohydrate moieties located outside of the hinge region. In another example, US Patent Application Publication 2007/0041979 discloses methods for preparing antibody molecules with enhanced resistance to proteases associated with disease processes by altering the glycosylation state of the antibody.

In one aspect of this invention, immunoglobulin from colostrum is fractionated on the basis of displayed carbohydrate to provide a preparation of antibody with improved stability to degradation in the digestive tract. It is known that bovine colostrum can be fractionated based on binding to jacalin. Jacalin is a lectin that recognizes alpha-O-glycoside of the disaccharide Thomsen-Friedenreich antigen (Gal beta1-3GalNAc), even in its sialylated form {Takahashi et al., 2006, Biochem Biophys Res Commun, 350, 580-7}. The jacalin-binding fraction is enriched in IgG1 and has increased stability to pepsin digestion compared to the non-binding fraction {Porto et al., 2007, J Dairy Sci, 90, 955-62}. Fractionation of colostrum based on jacalin binding has been explored in order to develop colostrum preparations that are more effective for feeding newborn calves. In one aspect of this invention, colostrum from immunized cows is fractionated for use as a human therapeutic.

Stabilized antibodies may be generated by the addition of moieties that sterically block the region or regions of the antibody molecule that are susceptible to enzymatic digestion. Preferably, these moieties are added to the hinge region. Stabilized antibodies may be generated by the addition of moieties that induce conformational changes in the antibody molecule such that the antibody is not susceptible to enzymatic attack. Stabilized antibodies may be generated by increasing or altering the expression of carbohydrates such as N-linked or O-linked carbohydrates that are inherently present on the antibody molecule due to normal cellular processes. Carbohydrates added to the hinge region are preferably O-linked. Carbohydrates added outside of the hinge region are preferably N-linked. Stabilized antibodies may be generated by adding N-linked or O-linked carbohydrates to the antibody molecule in vitro after the antibody has been synthesized. The moieties that confer stability may also be artificial entities such as polyethylene glycol.

Stabilized antibodies may be generated by the addition of one moiety that increases stability to gastric or oral degradation. Stabilized antibodies may be generated by the addition of multiple moieties that increase stability to gastric or oral degradation.

In one embodiment, antibody is fractionated based on the amount or type of carbohydrate moiety and the stability of the isolated fractions to gastric degradation or to degradation in the oral cavity are determined. Antibody may be fractionated using lectin-based chromatography or any other suitable technique known to those skilled in the art. These data are used to identify glycosylation patterns associated with stability.

In one embodiment the invention provides a method of enhancing the stability of an antibody to oral or gastric degradation by fractionating an antibody preparation based on binding to at least one lectin specific for at least one carbohydrate wherein the binding of that lectin has been shown to correspond with stability to gastric or oral degradation.

In one embodiment of this invention, a preparation of antibody is characterized based on the amount or type of glycan moiety for the purpose of predicting the proportion of antibody in the preparation with increased stability to gastric degradation or to degradation in the oral cavity. This characterization of antibody may be for the research and development purposes, for the purpose of setting specifications during the development process or for the purpose of in-process testing, release testing, or any other testing required for the manufacture of a commercial product. Characterization of glycan expression may be determined using any suitable technique known to those skilled in the art, including, but not limited to, ELISA, Western blotting, NMR, chromatography, electrophoresis, and mass spectrophotometry, including LC-MS, LC-MS/-MS, MALDI-TOF, TAMNDEM-MS, FTMS.

In one embodiment of this invention, antibody is collected from the milk or colostrum of immunized animals, preferably from the milk or colostrum of immunized cows. In one embodiment of this invention, bovine colostrum-derived antibody is fractionated based on binding to the lectin jacalin. In one embodiment of this invention, bovine colostrum-derived antibody is characterized based on the ability of the antibody to bind to the lectin jacalin. In one embodiment the invention provides a method of enhancing the stability of an antibody to oral or gastric degradation comprising the steps of:

a) collecting antibodies from the milk or colostrum of cow immunized with an antigen;
b) fractionating the antibodies of step (a) based on binding of the antibodies to the lectin jacalin; and optionally
c) assaying the fractions collected in step b), i) for stability to gastric or oral degradation, or ii) for the presence of carbohydrates associated with stability to gastric or oral degradation, or iii) for specific glycoforms associated with stability to gastric or oral degradation; and
d) selecting the fractions assayed comprising antibodies that are stabilized to gastric or oral degradation.

In one embodiment, bovine colostral immunoglobulin is fractionated using lectins specific for particular glycans and the fractions are assayed for their stability to gastric degradation and for their stability in the oral cavity. Lectins to be used in this invention include, but are not limited to, those isolated from *Agaricus bisporus, Amaranthus caudatus, Artocarpus heterophyllus, Artocarpus integrifolia, Griffonia simplicifolia lectin I, Griffonia simplicifolia lectin II, Griffonia simplicifolia I B4, Bauhinia purpurea alba, Codium fragile, Datura stramonium, Dolichos biflorus, Erythrina coralldendron, Euonymos europaeus, Glycine max, Helix aspersa, Helix pomatia, Hippeastrum hybrid, Lotus tetragonolobus, Lycopersicon esculentum, Maclura pomifera, Narcissus pseudonarcissus, Phaseolus vulgaris L, Phaseolus vulgaris E, Phytolacca Americana, Pisum sativum, Psophocarpus tetragonolobus I, Solanum tuberosum, Sophora japonica terminal, Maackia amurensis*, and *Wisteria floribunda*.

In one embodiment, stabilized antibody is generated by treatment with enzymes that add carbohydrate moieties to the antibody molecule. Suitable enzymes include, but are not limited to, O-GlcNAc-transferase, beta-1,4-galactosyltransferase, alpha-2,3-sialyltransferase and beta-1,4-N-acetylglucosaminyltransferase III. A further list of enzymes suitable for use in this invention is included in US Patent Application Publication 2007/0041979 and is incorporated herein. In one embodiment, the invention provides a method of enhancing the stability of an antibody to oral or gastric degradation comprising the steps of:

a) providing an antibody; and
b) reacting the antibody with enzymes that add carbohydrate moieties to the antibody molecule wherein the carbohydrate moieties increase stability of the antibody to oral or gastric degradation.

In one embodiment of this invention, stabilized antibodies are generated by engineering antibodies to express the hinge region sequence from bovine IgG1. Such antibodies are produced using methods described in U.S. Pat. No. 5,677,425. The hinge region of bovine IgG1 links the CH1 domain and the CH2 domain. Two allelic variants of bovine IgG1 are suitable for use in this invention: IgG1a: DPRCKTTCDCCPPPELPGG (SEQ ID NO. 1) and IgG1b: DPTCKPSPCDCCPPPELPGG (SEQ ID NO. 2). A third allelic variant, IgG1c: DPRCKRPCDCCPPPELPGG (SEQ ID NO. 3) would not be suitable for use in this invention due to the lack of serine and threonine residues in the hinge region.

In one embodiment, stabilized antibodies are generated by treating host animals or cell lines with hormones or other reagents to induce a change in immunoglobulin glycosylation. Although not intended to limit the invention through a particular mechanism, some of the stability of colostral immunoglobulin may result from changes in glycosylation induced by hormones or other factors associated with pregnancy or with lactation. These hormones or related reagents may be used to treat female animals, preferably pregnant animals, before or during parturition. Such hormones include, but are not limited to, adrenal glucocorticoids, thyroid hormones, prolactin, progesterone, estrogen, insulin and IGF-1, either alone or in combination.

In one embodiment, the invention provides a method of enhancing the stability of an antibody to degradation in the oral cavity or gastric degradation comprising the steps of:

a) treating an animal with a an agent that induces a change in immunoglobulin glycosylation; and
b) collecting antibody derived from the animal treated in step (a). In another embodiment, the invention provides a method of enhancing the stability of an antibody to degradation in the oral cavity or gastric degradation comprising the steps of:

a) treating an animal with a an agent that induces a change in immunoglobulin glycosylation;
b) collecting antibody derived from the animal treated in step (a);
c) fractionating the antibody collected in step b; and
d) assaying the fractions collected in step c), i) for stability to gastric or oral degradation, or ii) for the presence of carbohydrates associated with stability to gastric or oral degradation, or iii) for specific glycoforms associated with stability to gastric oral degradation.

The hormones or related reagents described above may also be used to treat cell lines used for the expression of immunoglobulin molecules to induce a change in immunoglobulin glycosylation that results in the generation of stabilized antibodies. Such hormones include, but are not limited to, adrenal glucocorticoids, thyroid hormones, prolactin, progesterone, estrogen, insulin and IGF-1, either alone or in combination. Although not intended to limit this invention to any particular cell line, monoclonal antibodies are currently produced using the following cell lines: Chinese Hamster Ovary (CHO), Mouse Myeloma (NSO, Sp2/0), Monkey Kidney (COS) and Baby Hamster Kidney (BHK) and all of these cell lines would be suitable in the use of this invention. In some aspects of this invention, prior to hormone treatment, cell lines may be transfected with the gene encoding O-GlcNAc transferase, or similar enzymes that facilitate appropriate glycosylation, including O-linked glycosylation of the antibody molecule.

In one embodiment, the invention provides a method of enhancing the stability of an antibody to degradation in the oral cavity or gastric degradation comprising the steps of:

a) contacting cell lines that are genetically engineered to produce immunoglobulin with an agent that induces a change in immunoglobulin glycosylation; and b) collecting antibody produced by the cell line of step (a). In another embodiment the invention provides a method of enhancing the stability of an antibody to degradation in the oral cavity or gastric degradation comprising the steps of:

a) contacting cell lines that are genetically engineered to produce immunoglobulin with an agent that induces a change in immunoglobulin glycosylation;

b) collecting antibody produced by the cell line of step (a);

c) fractionating the antibody collected in step (b);

d) assaying the fractions of step (c) for i) stability to gastric or oral degradation or ii) for the presence of carbohydrates associated with stability to gastric or oral degradation, or iii) for specific glycoforms associated with stability to gastric oral degradation; and optionally;

e) selecting the fractions comprising antibody that is stabilized to gastric or oral degradation. In one embodiment, methods may further include cells that are further genetically engineered to comprise genes encoding transferases that facilitate glycosylation of the immunoglobulin such as O-linked or N-linked glycosylation.

There is significant heterogeneity in levels and patterns of antibody glycosylation. This heterogeneity is observed in monoclonal antibody produced in tissue culture. This heterogeneity is also observed in polyclonal antibodies isolated from animals. As described in this application, differences in antibody glycosylation can affect the stability of antibodies to gastric digestion or to degradation in the oral cavity and differences in antibody glycosylation can further affect the mucosal permeability of antibodies. Therefore, different lots of antibody, whether isolated from animals or from cultured cells, are likely to display different levels of stability in the GI tract and different levels of mucosal permeability. In manufacturing therapeutic antibodies for topical application to the GI tract, variability in levels of stability or permeability would result in clinical materials with inconsistent potency. As a result, there is a need for analytical assays to test the glycosylation patterns of antibodies where those glycosylation patterns predict the stability of the antibodies in the digestive tract. There is also a need for methods to be used to apply these assays to the testing of different lots of antibody for the purpose of accepting or rejecting the particular lot of antibody in the manufacture of a drug product. It is also possible that during the manufacture of an antibody-based drug product (in steps including but not limited to purification, concentration, buffer exchange, lyophilization, spray drying, formulation and storage) changes in the pattern or level of antibody glycosylation may occur. As a result, there is a need for analytical assays to test the glycosylation patterns of antibodies to use in in-process testing, in release testing, and in stability assays.

In one embodiment of this invention antibody is tested for enhanced stability to gastric or oral degradation and/or enhanced mucosal permeability comprising the step of collecting an antibody preparation from an antibody source (e.g. milk or serum of immunized animal or monoclonal antibody cell culture or antibody-based final drug product), and testing for a property associated with enhanced stability to gastric or oral degradation (e.g. the amount and presence of O-linked glycosylation). In one embodiment, the antibody is tested for a property associated with enhanced stability or mucosal permeability in the digestive tract and compared to a standardized antibody preparation known to have enhanced stability or mucosal permeability the digestive tract. In one embodiment of this invention, samples from specific lots of milk or colostrum from immunized animals are tested to quantify the amount and pattern of glycosylation, where the glycosylation pattern is associated with the stability of the antibody in the digestive tract and/or with mucosal permeability e.g. the amount and presence of O-linked glycosylation. The test results are used to determine whether those lots should be accepted for inclusion in a product. In one embodiment of this invention, samples from specific lots of serum from immunized animals are tested to quantify the amount and pattern of glycosylation where the glycosylation pattern is associated with the stability of the antibody in the digestive tract and/or with mucosal permeability. The test results are used to determine whether those lots should be accepted for inclusion in a product. In one embodiment of this invention, samples from specific lots of cell supernatant from cell cultures expressing monoclonal antibodies are tested to quantify the amount and pattern of glycosylation where the glycosylation pattern is associated with the stability of the antibody in the digestive tract and/or with mucosal permeability. The test results are used to determine whether those lots should be accepted for inclusion in a product. In one embodiment of this invention, in-process samples collected during the manufacture of an antibody product are tested to quantify the amount and pattern of glycosylation where the glycosylation pattern is associated with the stability of the antibody in the digestive tract and/or with mucosal permeability. The test results are used to determine whether the manufacturing process is within the pre-defined specifications and whether the antibody should be accepted or rejected. In one embodiment of this invention, samples are collected from the final drug substance or drug product that results from the manufacture of an antibody product are tested to quantify the amount and pattern of glycosylation where the glycosylation pattern is associated with the stability of the antibody in the digestive tract and/or with mucosal permeability. The test results are used to determine whether the drug substance or drug product meets specifications and can be released for the final commercial product.

Stabilized antibodies may be used in the oral cavity for the prevention of dental caries and for the treatment or prevention of periodontal disease as described in U.S. Pat. Nos. 5,759,544; 4,689,221; 4,324,782; 4,693,888; 4,725,428; 6,143,330; 5,240,704 and 5,352,446, for the control of microorganisms, including bacteria, protozoa, parasites, viruses and fungi, or for the control of inflammation through the use of antibodies specific for cytokines or chemokines, or receptors for cytokines or chemokines. Stabilized antibodies used in the oral cavity may be specific for receptors or other antigens expressed on the apical surface of the oral cavity, against receptors or other antigens expressed on the basolateral surface of the mucosal barrier of the oral cavity, or against receptors or other antigens expressed in the mucosa, submucosa, or any other region of the body accessible to topically applied antibody. Such antibodies may be used for the treatment of infections of the oral cavity or diseases of the oral cavity, including but not limited to mucositis, cancers of the oral cavity, nicotinic stomatitis, leukoplakia, hairy tongue, recurrent aphthous stomatitis, geographic tongue, denture stomatitis, gastroesophageal reflux, eosinophilic esophagitis and lichen planus. Antibodies may also be applied topically to the oral cavity as a diagnostic reagent as described in U.S. Pat. No. 7,175,430.

Many of the proteases present in the oral cavity are of bacterial origin. In one embodiment of this invention, a topical antibiotic is administered to the oral cavity prior to topical administration of antibody. In one embodiment of this invention, protease inhibitors are administered to the oral cavity prior to and/or concurrently with topical administration of antibody. Microbes in the oral cavity also produce hydrolases that remove carbohydrate from antibody, thus making it more susceptible to proteolytic degradation. In one embodiment of this invention, hydrolase inhibitors are administered to the oral cavity prior to and/or concurrently with topical administration of antibody. Antibiotics, protease inhibitors and hydrolase inhibitors may be given in combination.

Stabilized antibodies may be used in the GI tract for the treatment or prevention of diseases, including but not limited to bacterial, viral or parasitic infections of the gastrointestinal tract, cancers of the gastrointestinal tract, inflammation of the gastrointestinal tract as a result of injury, surgery, radiation, infection or autoimmune disease.

Stabilized antibodies are useful in the modulation of apical receptors in the digestive tract, including nutrient receptors, nutrient transporters, pattern recognition receptors, chemokine receptors, cytokine receptors, bile salt transporters, inorganic ion transporters, mineral transporters, peptidases, saccharases, and growth factor receptors.

Stabilized antibodies are useful in the treatment or prevention of food allergies or intolerances, including celiac disease. In one embodiment, a stabilized antibody for treatment of celiac disease is specific for gluten or gluten derived peptides.

Stabilized antibodies are useful in modulating the function of receptors, cytokines, chemokines or similar mediators expressed in the lumen of the digestive tract or, in the case of a disease or condition that renders the digestive tract permeable to topically applied antibodies, in modulating the function of receptors, cytokines, chemokines or similar mediators expressed in the portions of the body below the mucosal barrier that are accessible to the antibody. Stabilized antibodies are useful in the treatment of immunodeficiency.

When combined with a suitable delivery vehicle, stabilized antibodies are useful for systemic dosing.

It is understood by one skilled in the art that antibody fragments are also subject to degradation in the digestive tract and may be processed using any of the suitable techniques described in this application to increase their stability to degradation in the digestive tract. It is understood by one skilled in the art that molecules designed to mimic the activity of antibodies are also subject to degradation in the digestive tract and may be processed using any of the suitable techniques described in this application to increase their stability to degradation in the digestive tract.

Antibody Administration to Patients with Compromised Mucosal Barrier in the Digestive Tract.

In the normally functioning digestive tract, intact protein cannot cross the mucosal barrier. Small amounts of protein are taken up as part of antigen sampling by the immune system, but this protein is degraded during antigen processing and does not retain activity. As a result, topical application of an antibody therapeutic to the digestive tract can only access target antigens that are expressed within the lumen of the digestive tract or on the luminal surface of the digestive tract. However, in some disease states, the integrity of the barrier function is compromised. In this invention, this altered barrier function is exploited to permit therapeutic antibodies applied to the oral cavity or the lumen of the digestive tract to penetrate the mucosal barrier.

There are 4 elements that bear on the permeability of the digestive tract and the ability of topically applied antibody to penetrate the mucosal barrier. First, the area of the digestive tract is an important factor, as the mucosal barrier is made up of different cell types at different portions of the digestive tract. The hard palate and gingiva in the mouth are lined with keratinized, stratified, squamous epithelium. The soft palate, floor of mouth, cheek, underside of tongue and inside of lips are lined with non-keratinized stratified squamous epithelium. The tongue is a complex mixture of keratinized and non-keratinized stratified squamous epithelium. The oropharynx is lined with a non-keratinized, stratified, squamous epithelium. The esophagus is lined with stratified, squamous epithelium and has numerous mucus glands. From the lower esophageal sphincter down to the anus, there is a single contiguous layer of epithelial cells joined by tight junctions. The small intestine, consisting of the duodenum, the jejunum and the ileum, contains numerous finger-like projections called villi. The bases of the villi contain crypts with undifferentiated stem cells. The epithelium consists mainly of simple columnar epithelial cells, absorptive cells and mucus-secreting goblet cells. The large intestine, consisting of the cecum, colon (ascending, transverse, descending, and sigmoid), rectum, and anal canal, differs from the small intestine in that it does not contain permanent folds or villi. These various tissues are known to differ in their permeability to both small molecules and to proteins {Squier, 1991, Crit. Rev Oral Biol Med, 2, 13-32}.

Second, the nature of the insult that causes the barrier defect is an important element. Changes in permeability may result from trauma, irritation, injury from chemicals, radiation or burn, exposure to bile, ischemia, reperfusion injury, inflammation, or infection. Increased permeability can result from frank destruction of the mucosa, as in the case of acute trauma (although it should be noted that epithelial restitution begins in minutes, and fibrin clots and other pseudomembranes form rapidly over traumatic ulcers; thus, even antibody accessibility to open wounds necessitates antibody transit through biological barriers). Increased permeability of the digestive tract can occur through increased paracellular or transcellular transport, where paracellular transport is the transport of material through the tight junctions of the epithelium and transcellular transport is the transport of material through the cells of the epithelium. Both of these processes are highly regulated and affected differently by different factors. For example, paracellular transport is differentially affected by the inflammatory cytokines TNF, TGF-beta and IFN-gamma (IFN-γ) and by infection with enteropathogenic *E. coli* {Shen and Turner, 2006, Am J Physiol Gastrointest Liver Physiol, 290, G577-82}. In another example, a direct comparison of traumatic ulcers and recurrent aphthous ulcers revealed that they healed at different rates and were characterized by different patterns of expression of inflammatory mediators {Natah et al., 2000, J Oral Pathol Med, 29, 19-25}.

Third, the underlying health of the individual and tissue that have suffered the insult is an important element, because it will affect the healing process. There are at least 3 mechanisms involved in healing a breach in the mucosal barrier {Sturm and Dignass, 2008, World J Gastroenterol, 14, 348-53}. As per the first mechanism, epithelial restitution begins within minutes, with epithelial cells adjacent to the injured surface migrating into the wound. Second, epithelial cell proliferate to replenish the decreased cell pool. Third, undifferentiated epithelial cells mature and differentiate to maintain the many functional activities of the mucosal epithelium. The healing of the injury is regulated by cytokines, growth factors, adhesion molecules, neuropeptides and phospholipids. While inflammation is an essential element in the repair of any wound, inflammation may also interfere with these processes, particularly the early stages of epithelial restitution. Therefore, the abnormal immune system found in individuals with autoimmune disease, will alter the rate and ability of the lesion to heal. Similarly, the presence of chronic inflammation will alter the rate and ability of the lesion to heal.

Fourth, the nature of the antibody particularly the glycosylation pattern of the antibody, will affect the ability of the antibody to cross a damaged mucosal membrane. Glycosylation of the antibody will affect both its ability to interact with membrane-associated proteins, and its overall charge. The charge on the protein may affect the ability of the antibody to cross the mucosal membrane. In one aspect of this invention, antibodies with enhanced mucosal permeability are preferred for the treatment of patients with compromised mucosal barriers.

Mucositis

Mucositis, also known as stomatitits, can occur as a result of chemotherapy or radiation therapy, either alone or in combination. For the purposes of this application, mucositis also includes damage caused by exposure to radiation outside of the context of radiation therapy. Chemotherapeutic agents which may induce mucositis when used alone or in combination include, but are not limited to, platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

As used herein "to treat", "treating" or "treatment" as it relates to mucositis includes prophylactic and preventative treatment as well as treatment of ongoing disease. For the prevention of mucositis, for example, the antibodies of the invention can be administered prior to initiation of a cycle, for example, of chemotherapy and/or radiation therapy. Alternatively, the antibodies can be administered concurrently with, a cycle, for example of chemotherapy and/or radiation therapy. Alternatively, the antibodies can be administered prior to and concurrently with a cycle, for example, of chemotherapy and/or radiation therapy. For the treatment of mucositis, for example, the antibodies of the invention can be administered concurrently with a cycle, for example, of chemotherapy and/or radiation therapy. Alternatively, the antibodies can be administered following the completion of a cycle, for example, of chemotherapy and/or radiation therapy. Alternatively, the antibodies can be administered concurrently with and following the completion of a cycle, for example, chemotherapy and/or radiation therapy. The antibodies in this invention can be used in combination with other local or systemic therapies that are in use or will be developed for the treatment or prevention of mucositis.

In one preferred embodiment, anti-TNF antibodies are used to treat or prevent mucositis. In one embodiment, the invention provides a method of treating mucositis in a patient comprising administering to the patient a composition comprising a therapeutically effective amount of an antibody specific for tumor necrosis factor (TNF). In one embodiment, the anti-TNF antibody is a stabilized antibody of the invention and/or is an antibody with enhanced mucosal permeability. In another embodiment, the anti-TNF antibody is administered topically to the oral cavity, or topically to the GI tract as described herein. In one embodiment, the anti-TNF antibody is administered by parenteral administration. In one embodiment, the anti-TNF antibody is a polyclonal antibody, a monoclonal antibody, a humanized antibody, a chimerized antibody, or an antibody fragment or synthetic molecule designed to mimic the function of an antibody as described herein. In one aspect of this embodiment, the anti-TNF antibody is a polyclonal antibody derived from the milk or colostrum of a cow.

Other Diseases Associated with Altered Permeability of the Digestive Tract

In one embodiment, the invention provides a method of delivering an antibody to the oral cavity of a patient comprising topically administering the antibody to the oral cavity of the patient, wherein the mucosal barrier of the patient's oral cavity is compromised such that it is permeable to the antibody and wherein the antibody is directed at targets expressed below the mucosal barrier of the oral cavity. In one embodiment, a topical antibiotic, a protease inhibitor, hydrolase inhibitor or any combination thereof is administered to the oral cavity prior to, or concurrently with the topical administration of antibody. In one embodiment, the antibody is a stabilized antibody of the invention. In one embodiment, the antibody is an antibody with enhanced mucosal permeability. In one embodiment, the antibody is administered by buccal, gingival or sublingual administration in a suitable dosage form for such administration. Suitable dosage forms for use in the oral cavity include but are not limited to: buccal patches, buccal tape, mucoadhesive films, sublingual tablets, lozenges, wafers, chewable tablets, quick or fast dissolving tablets, effervescent tablets, a buccal or sublingual solid, granules, sprinkles, pellets, beads, powders, suspensions a mouthwash, gels.

In one embodiment, the invention provides a method of delivering an antibody to the digestive tract of a patient comprising contacting the antibody with the digestive tract of the patient wherein the mucosal barrier of the patient's digestive tract is compromised such that it is permeable to the antibody, wherein the antibody is directed at targets expressed below the mucosal barrier and wherein the patient is not suffering from a chronically dysregulated immune system as a result of immaturity or an autoimmune disease that targets the digestive tract. As used herein, a "chronically dysregulated immune system as a result of immaturity" includes but is not limited to conditions such as necrotizing enterocolotis. As used herein the term "autoimmune diseases that target the GI tract" includes but is not limited to inflammatory bowel disease (IBD), diabetes, and systemic lupis erythematoses (SLE).

In one embodiment, the invention provides a method of delivering a stabilized antibody to the digestive tract of a patient comprising contacting the antibody with the digestive tract of the patient wherein the patient's digestive tract is compromised such that it is permeable to the antibody, wherein the antibody is directed at targets expressed below the mucosal surface. In one embodiment, the stabilized antibody is enriched for least one carbohydrate moiety. In another embodiment, the antibody is stabilized by adding one or more carbohydrate moieties to the antibody after the antibody has been synthesized. In one embodiment the antibody is stabilized by treatment with enzymes to add carbohydrate molecules to the antibody. In one embodiment, the antibody is a stabilized antibody that has been genetically engineered to express the hinge region sequence from bovine IgG1.

In accordance with the methods of the invention, the mucosal barrier of the digestive tract may be breached or compromised through mechanical trauma, including but not limited to dental and oral wounds, esophageal wounds, or surgically induced trauma due to partial gut resection, jejunostomy, ileostomy, colostomy or other surgical procedures. The mucosal barrier of the digestive tract may also be breached by ischemia or reperfusion injury.

The mucosal barrier of the digestive tract may be breached or compromised through gross inflammation and/or ulceration, including but not limited to periodontal disease, aphthous stomatitis bacterial, viral, fungal or parasitic infections of the digestive tract, peptic ulcers, ulcers associated with stress or *H. pylori* infection, damage caused by esophageal reflux, inflammatory bowel disease, damage caused by cancer of the digestive tract, food intolerance, including celiac disease, or ulcers induced by NSAIDs or other ingested or systemically delivered drugs.

Patients with irritable bowel syndrome have altered intestinal permeability despite having little or no detectable histological changes in the intestines (Dunlop SP Am J. Gastroenterol. 2006 June; 101(6):1288-94). Patients with celiac disease have altered intestinal permeability and characteristic damage to the villi of the small intestine that is distinguishable from IBD.

Inflammatory bowel disease is thought to result from a dysregulated immune response initiated by microbial-host interactions. The immune system responds to non-pathogenic commensal bacteria generating chronic inflammation. Similarly, in necrotizing enterocolitis, a stressed underdeveloped immune system generates an inappropriate response to normal intestinal bacteria, inducing a potentially fatal form of colitis Pilling et al., 2006, J Immunol, 177, 3273-82}.

The breach in or compromise of the mucosal barrier of the digestive tract may be one that has been described clinically but where the biological basis for the barrier defect is not well understood, including but not limited to the loss of gut barrier function associated with external burns, trauma, sepsis or shock, irritable bowel syndrome, diabetes (in particular type I diabetes), atopic dermatitis, patients suffering from autoimmune disorders, including ankylosing spondylitis, Sjogren's syndrome, congestive heart failure, or multiple sclerosis. Infections with pathogens may also cause specific disruptions of barrier function.

In some diseases or disorders to which this invention may be applied, altered barrier permeability may be present prior to the development of frank inflammation and/or ulceration and antibodies may be applied at the time of altered barrier permeability as well as during the time of inflammation and ulceration. Diseases and disorders which include increased permeability prior to inflammation include but are not limited to mucositis induced by chemotherapy or radiation therapy, inflammatory bowel disease and celiac disease.

In some diseases or disorders to which this invention may be applied, altered barrier permeability may be present at discrete portions of the digestive tract while frank inflammation and/or ulceration is present at other portions of the digestive tract {Soderholm et al., 2004, Gut, 53, 1817-24}. Diseases and disorders which include physically separated regions of increased permeability and inflammation or ulceration include but are not limited to Crohn's disease and ulcerative colitis. Antibodies of this invention may be used to access the regions of altered permeability as well as the regions of frank inflammation and ulceration.

This invention includes the use of antibodies as therapeutics that are designed to address the underlying cause of the barrier defect. Such antibodies may be directed at biological targets that enhance wound healing, that alter the function of tight junctions, or at other targets known now or in the future that affect permeability. Suitable targets may include but are not limited to occludin, claudins, junctional adhesion molecule, ZO-1, E-cadherin, coxackie adenovirus receptor and serine proteases such as elastase that are involved in the release of claudins.

This invention includes the use of antibodies as therapeutics that are designed to bind to biological targets unrelated to the underlying cause of the barrier defect. Such antibodies may be used to treat or prevent diseases and disorders relating to the same disease state that caused the barrier defect. Such antibodies may be used to treat or prevent diseases and disorders unrelated to the disease state that caused the barrier defect.

This invention includes the use of antibodies directed at biological targets expressed on the basal side of the epithelium, targets expressed in the submucosa, target expressed in the lateral intercellular space, targets expressed in the lamina propria, targets expressed in the central nervous system, targets expressed in the systemic circulation and targets expressed in any region of the body that is accessible to delivered antibody as a result of damaged barrier function.

This invention includes the use of antibodies that are also known to be effective when administered by injection or infusion for systemic exposure. For example, systemically administered anti-TNF antibodies are effective in the treatment of inflammatory bowel disease {Kozuch and Hanauer, 2008, World J Gastroenterol, 14, 354-77}, recurrent aphthous stomatitis {Vujevich and Zirwas, 2005, Cutis, 76, 129-32}, and Behcet's disease {Almoznino and Ben-Chemit, 2007, Clin Exp Rheumatol, 25, S99-102}. The antibodies of this invention may be more efficacious when administered topically or topical application may result in reduced side effects. Topical application may also be preferred, even in the absence of superior efficacy or side effect profile, because of increased ease of administration. This invention includes the use of antibodies that have not been shown to be effective or are not effective when administered by injection or infusion for systemic exposure.

For the treatment of aphthous stomatitis (RAS), the antibodies of the invention can be administered at the earliest manifestation of an ulcer. Alternatively, the antibodies can be administered on a regular basis throughout the course of manifestation of the ulcer. Alternatively, the antibodies can be administered on a regular basis to prevent the recurrence of ulcer formation. In one preferred embodiment, the invention provides a method of treating recurrent aphthous stomatitis (RAS) in a patient comprising administering to the patient by topical application to the oral cavity a therapeutically effective amount of a composition comprising an antibody specific for TNF (an anti-TNF antibody). In one embodiment the anti-TNF antibody is a stabilized antibody of the invention. In one embodiment the anti-TNF antibody is an antibody with enhanced mucosal permeability. In another embodiment anti-TNF antibody is administered topically to the oral cavity as described herein. In one embodiment, the anti-TNF antibody is a polyclonal antibody, a monoclonal antibody, a humanized antibody, a chimerized antibody, or an antibody fragment or synthetic molecule designed to mimic the function of an antibody as described herein.

In one embodiment of the invention, antibodies are not targeted to exogenous agents, where "exogenous agents" are defined as those agents that are not synthesized in the body of the animal being treated with the antibodies. Agents that are synthesized by microorganisms resident in the body of the animal being treated with the antibodies are considered exogenous agents. Biological targets of the antibodies of the invention are preferably endogenous to the organism being administered the antibody.

In one embodiment of the invention, antibodies are not targeted to infectious agents, including viruses, bacteria, fungi, protozoa and parasites.

In one embodiment of the invention, antibodies are not targeted to antigens expressed in the lumen of the digestive tract or on the luminal aspect of the digestive tract epithelium.

In one embodiment of the invention, antibodies specific for inflammatory cytokines, including but not limited to TNF, TNF-kappa, IL-6, Ifn-gamma, IL-1 beta, IL-12, IL-13, IL-23, IL-17 and IL-2 are applied topically to the digestive tract of a patient with increased permeability of the digestive tract to prevent the development of frank ulceration or inflammation due to chemotherapy or radiation therapy.

In one embodiment of the invention, antibodies specific for inflammatory cytokines, including but not limited to TNF, TNF-kappa, IL-6, Ifn-gamma, IL-1 beta, IL-12, IL-13, IL-23, IL-17 and IL-2 are applied topically to the digestive tract of a patient with increased permeability of the digestive track to prevent the development of frank ulceration or inflammation due to autoimmune disease, including inflammatory bowel disease.

In one embodiment of the invention, antibodies specific for Toll-like receptors that are expressed on the basolateral face of mucosal epithelial cells are applied as a therapeutic agent to the digestive tract of a patient with an intestinal inflammatory disease.

In one embodiment of the invention, antibodies specific for inflammatory cytokines, including but not limited to TNF, TNF-kappa, IL-6, Ifn-gamma, IL-1 beta, IL-12, IL-13, IL-23, IL-17 and IL-2 are applied as a therapeutic agent to the digestive tract of a patient with irritable bowel syndrome.

In one embodiment of the invention, antibodies directed at enteric neurotransmitters or their receptors or transporters expressed below the mucosal barrier of the digestive tract, including receptors for serotonin that are expressed in the gut (5-HT1A, 5-HT1B/B, 5-HT2A, 5-HT2B, 5-HT3,5-HT4,5-HT7,5-HT1P {De Ponti, 2004, Gut, 53, 1520-35}) are used as pharmaceutical agents in patients with increased digestive tract permeability.

In one embodiment of the invention, antibodies directed at peptides that regulate food intake or the receptors for such peptides are used as pharmaceutical agents in patients with increased digestive tract permeability. Such peptides include but are not limited to CCK, GLP1, GIP, oxyntomodulin, PYY3-36, enterostatin, APOAIV, PP, amylin, GRP and NMB, gastric leptin and ghrelin {Cummings and Overduin, 2007, J Clin Invest, 117, 13-23}.

In one embodiment of the invention, antibodies directed at epidermal growth factor receptor on colorectal cancer cells are used as therapeutic agents in patients with increased digestive tract permeability.

In one embodiment of the invention, patients suffering from radiation exposure, trauma, burn, shock or sepsis are treated orally with antibodies directed against infectious agents, inflammatory cytokines, including but not limited to TNF-alpha. In one embodiment, the antibody is not targeted to TNF when the disease is Crohn's Disease or Ulcerative Colitis.

Patients suitable for application of this invention are identified by direct measurement of digestive tract permeability, by diagnosis with a disease associated with increased digestive tract permeability, by detection of a genetic marker or biomarker associated with increased digestive tract permeability, by known or presumed exposure to an agent known to induce increased digestive tract permeability or by genetic relationship with an individual known to have or be at risk for increased digestive tract permeability. U.S. Pat. No. 6,037,330 teaches methods to detect damage to specific portions of the digestive tract that manifest as increased permeability.

It is known in the art that the permeability of the digestive tract can be intentionally increased for the purposes of drug delivery. Permeation enhancers are available, including chitosan, poly-L-arginine and Carbopol, which have been used to enhance buccal absorption of pharmaceuticals. U.S. Pat. No. 5,849,322 teaches methods to enhance buccal delivery of therapeutics. U.S. Pat. No. 5,665,389 teaches the intentional enhancement of intestinal permeability for the purposes of delivering insulin to the systemic circulation. In none of these teachings has the increased permeability associated with the disease state been exploited for the purposes of delivering an antibody, a protein, or any other therapeutic agent. The methods of the present invention include the use of such permeation enhancers to enhance the delivery of antibody to the digestive tract.

As discussed earlier, the nature of the antibody particularly the glycosylation pattern of the antibody, will affect the ability of the antibody to cross a damaged mucosal membrane. Glycosylation of the antibody will affect both its ability to interact with membrane-associated proteins, and its overall charge. The charge on the protein may affect the ability of the antibody to cross the mucosal membrane. In one aspect of this invention, antibodies with defined glycosylation patterns conferring enhanced mucosal permeability on the antibodies are preferred for the treatment of patients with compromised mucosal barriers.

In one embodiment, the invention provides antibodies with enhanced mucosal permeability. Preferably the antibody comprises enhanced mucosal permeability in a compromised digestive tract. Antibodies comprising enhanced mucosal permeability include monoclonal antibodies, polyclonal antibodies, and/or any other antibody as described herein. In one embodiment, the antibody is enriched for at least one glycoform that confers enhanced mucosal permeability. In one embodiment, the glycoform contains oligomannose or sialic acid. In one embodiment, the glycoform does not contain oligomannose or sialic acid. In one embodiment, the antibody has been treated with enzymes to add or remove carbohydrates that confer enhanced permeability after the antibody has been synthesized. In another embodiment, the antibody having enhanced mucosal permeability is also a stabilized antibody comprising enhanced stability to oral or gastric degradation as described herein.

In one embodiment, the invention provides a method of delivering an antibody to the digestive tract of a patient comprising contacting the antibody with the digestive tract of the patient wherein the mucosal barrier of the patient's digestive tract is compromised such that it is permeable to the antibody, and wherein the antibody is directed at targets expressed below the mucosal barrier and wherein the antibody comprises a glycosylation pattern that enhances the antibody's ability to cross the permeable mucosal barrier of the compromised digestive tract. In one embodiment, antibody is tested for enhanced permeability, particularly enhanced permeability in a compromised digestive tract, comprising the step of collecting an antibody preparation from an antibody source (e.g. milk or serum of immunized animal or monoclonal antibody cell culture) and testing the antibody preparation for a property associated with enhanced permeability in a compromised digestive tract e.g. the amount and pattern of O-linked glycosylation. In one embodiment of this invention, samples from specific lots of milk or colostrum from immunized animals are tested to quantify the amount and pattern of glycosylation, where the glycosylation pattern is associated with enhanced mucosal permeability in a compromised digestive tract e.g. the amount and pattern of O-linked glycosylation. In one embodiment, the antibody is tested for a property associated with enhanced mucosal permeability in a compromised digestive tract and compared to a standardized antibody preparation known to have enhanced mucosal permeability in a compromised digestive tract.

In one embodiment the invention provides a method of identifying antibodies having enhanced mucosal permeability in a compromised digestive tract comprising the steps of:

a) fractionating an antibody preparation to provide separate antibody preparations each with a different pattern of glycosylation; and b) assaying the antibody preparations of step (a) for enhanced ability to cross the permeable mucosal barrier of a compromised digestive tract.

In one preferred embodiment, the invention provides a method of treating inflammatory bowel disease (IBD) or Crohn's disease in a patient comprising administering to the patient a composition comprising a therapeutically effective amount of an antibody specific for tumor necrosis factor (TNF) wherein the antibody comprises a glycosylation pattern that enhances the ability of the antibody to cross the permeable mucosal barrier of a patient suffering from IBD or Crohn's disease. In one aspect of this embodiment the antibody is a polyclonal antibody derived from the milk or colostrum of a cow.

For disorders of the oral cavity, the antibodies of the invention can be delivered in a mouthwash, rinse, paste, gel, or other suitable formulation. Antibodies of the invention can be delivered using formulations designed to increase the contact between the active antibody and the mucosal surface, such as buccal patches, buccal tape, mucoadhesive films, sublingual tablets, lozenges, wafers, chewable tablets, quick or fast dissolving tablets, effervescent tablets, or a buccal or sublingual solid. For disorders of the GI tract, antibody can be delivered by oral ingestion in the form of a capsule, tablet, liquid formulation or similar form designed to introduce drug to the GI tract. Alternatively, antibody may be administered by suppository or enema for delivery to the lower GI tract. Such formulations are well known to those skilled in the art. These routes of administration and dosage forms are discussed in detail herein.

Antibodies

The terms "antibody" or "antibodies" as used herein refer to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding to a target receptor. An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by degradation with various peptidases that are able to compete with the intact antibody for specific binding, unless otherwise specified herein. Thus, for example, pepsin digests an antibody below the disulfide linkages in the hinge region to produce $F(ab)'_2$, a dimer of Fab which itself is a light chain joined to $V_{H-CH}1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the degradation of an intact antibody, one of skill will appreciate that such fragments may be synthesized de novo either chemically or by using recombinant DNA methodology. Thus, the term "antibody", as used herein, also includes antibody fragments either produced by the modification of whole antibodies, or those synthesized de novo using chemical or recombinant DNA methodologies (e.g., single chain Fv, complementarity determining region (CDR) fragments, or polypeptides that contain at least a portion of an immunoglobulin that is sufficient to confer specific receptor binding to the polypeptide) or those identified using phage display libraries (see, e.g., McCafferty et al., *Nature* 348: 552-554 (1990)).

The terms "monoclonal antibody" or "monoclonal antibodies" as used herein refer to a preparation of antibodies of single molecular composition. A monoclonal antibody composition displays a single binding specificity and affinity for a particular epitope of a target receptor.

An "epitope" is the portion of a molecule that is bound by an antibody. An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antibody).

The term "polyclonal antibody" as used herein refers to a composition of different antibody molecules which is capable of binding to or reacting with several different specific antigenic determinants on the same or on different antigens. The variability in antigen specificity of a polyclonal antibody is located in the variable regions of the individual antibodies constituting the polyclonal antibody, in particular in the complementarity determining regions (CDR)1, CDR2 and CDR3 regions. Preferably, the polyclonal antibody is prepared by immunization of an animal with the target antigen or portions thereof as specified below. Alternatively, the polyclonal antibody may be prepared by mixing multiple monoclonal antibodies (e.g. Nowakowski, A. et al. 2002. Proc Natl Acad Sci USA 99, 11346-11350 and U.S. Pat. No. 5,126,130) having desired specificity to a target receptor.

Polyclonal antibody preparations isolated from the blood, milk, colostrum or eggs of immunized animals typically include antibodies that are not specific for the immunogen in addition to antibodies specific for the target receptor. Antibodies specific for the target receptor may be purified from the polyclonal antibody preparation or the polyclonal antibody preparation may be used without further purification. Thus, the term "polyclonal antibody" as used herein refers both to antibody preparations in which the antibody specific for the target receptor has been enriched and to preparations that are not purified. Numerous techniques are known to those in the art for enriching polyclonal antibodies for antibodies to specific targets. A technology for recombinant production of highly specific polyclonal antibodies suitable for prophylactic and therapeutic administration has been developed (WO 2004/061104). The recombinant polyclonal antibody (rpAb) can be purified from a production bioreactor as a single preparation without separate handling, manufacturing, purification, or characterization of the individual members constituting the recombinant polyclonal protein.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. See, e.g., U.S. Pat. No. 4,816,567 and Morrison, 1985, *Science* 229:1202-07.

The invention further contemplates the use of molecules intended to mimic antibodies, such as aptamers. The invention also contemplates the use of "fusion proteins" in which a portion of an antibody molecule is fused to the ligand for the target receptor and thereby made specific for the target receptor. In another aspect, the present invention provides a derivative of an antibody specific for a target antigen. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols.

Derivitized antibodies are also suitable for in-vivo or in-vitro detection of expression of a target. In one preferred embodiment, an antibody derivitized with a physiologically acceptable label detectable by standard imaging equipment such as ultrasound, is used for in-vivo diagnostic imaging to detect aberrant expression of a target. Such diagnostic techniques are useful in identifying patients who have elevated expression, activation or activity of a target associated with one or more diseases thereby identifying patients who may benefit most from treatment with an antibody of the invention.

The present invention further comprises nucleic acid molecules encoding all or a part of an antibody of the invention, for example, one or both chains of the antibody of the invention or a fragment, derivative, or variation thereof. The nucleic acids can be single-stranded or double stranded and can comprise RNA and/or DNA nucleotides or variants there of such as peptide nucleic acids. The present invention further comprises host cells into which a recombinant expression vector or transfectoma is introduced and is capable of expressing an antibody of the invention or fragment thereof. A host cell can be any prokaryotic cell or eukaryotic cell. Vector DNA can be introduced into a host cell via conventional transformation or transfection techniques.

In one embodiment, the antibody of the invention is capable of at least partially blocking at least one biological activity of a target antigen. In another embodiment, the antibody of the invention has a binding affinity ($K_a$) for the target receptor of at least $10^6$. In other embodiments, the antibody exhibits a $K_a$ of at least $10^7$, at least $10^8$, at least $10^9$, or at least $10^{10}$. In another embodiment, the present invention provides an antibody that has a low dissociation rate from a target antigen. In one embodiment, the antibody has a $K_{off}$ of $1 \times 10^{-4}$ $s^{-1}$ or lower. In another embodiment, the $K_{off}$ is $5 \times 10^{-5}$ $s^{-1}$ or lower. It is understood by those skilled in the art that these affinities and dissociation rates refer to average affinities and dissociation rates when used to describe polyclonal antibodies. It is further understood by those skilled in the art that affinity is defined broadly and includes avidity as well as affinity. In another aspect, the present invention provides an antibody that inhibits at least one biological activity of a target antigen. In one embodiment, the antibody has an $IC_{50}$ of 1000 nM or lower. In another embodiment, the $IC_{50}$ is 100 nM or lower; in another embodiment, the $IC_{50}$ is 10 nM or lower.

In one embodiment, monoclonal antibodies are preferred. In another embodiment polyclonal antibodies are preferred. Monoclonal antibodies are more controllable, but their specificity is limited. Polyclonal antibodies are more difficult to characterize, but their broad specificity means that they can interfere with target receptors in several different ways. In addition, the manufacture of polyclonal antibodies can be very inexpensive.

Methods of producing polyclonal and monoclonal antibodies that react specifically with the target antigens of the invention are known to those of skill in the art (see, e.g., Coligan, *Current Protocols in Immunology* (1991); Harlow & Lane, Antibodies, A Laboratory Manual (1988); Goding, *Monoclonal Antibodies: Principles and Practice* (2d ed. 1986); and Kohler & Milstein, *Nature* 256: 495-497 (1975). Such techniques include antibody preparation by selection of antibodies from libraries of recombinant antibodies in phage or similar vectors, as well as preparation of polyclonal and monoclonal antibodies by immunizing suitable animals (see, e.g., Huse et al., *Science* 246: 1275-1281 (1989); Ward et al., *Nature* 341: 544-546 (1989)).

A number of immunogens comprising target antigens or portions of target antigens may be used to produce antibodies specifically reactive with the target antigen. For example, an antigenic fragment or protein portion of a target antigen can be isolated using known procedures. Recombinant protein can be expressed in eukaryotic or prokaryotic cells as described above, and purified as generally described above. Alternatively, a synthetic peptide derived from a target antigen can be used as an immunogen. Preferably, the peptide is derived from a portion of the target antigen that is expressed extracellularly. The synthetic peptide may be conjugated to a carrier protein prior to immunization. Naturally occurring protein may also be used either in pure or impure form. The product is then injected into an animal capable of producing antibodies. Animals may also be immunized with cells that have been transfected with the target antigen or may be immunized with DNA encoding the target antigen. Either monoclonal or polyclonal antibodies may be generated accordingly.

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, Eur. J. Immunol. 6: 511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246: 1275-1281 (1989).

Methods of production of polyclonal antibodies are known to those of skill in the art. An appropriate animal is immunized with the protein using a standard adjuvant, such as Freund's adjuvant, and a standard immunization protocol. The animal's immune response to the immunogen preparation may be monitored by taking test bleeds and determining the titer of reactivity to target receptor. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Alternatively, eggs can be collected from immunized birds and antibody is isolated from the yolks of the eggs. Alternatively, milk or colostrum can be collected from immunized female animals and antibody is isolated from the milk or colostrum.

In one embodiment the antibody is isolated from the yolk of eggs from a bird such as a chicken, duck, or goose that has been immunized with a target antigen and/or peptide or antigenic portion derived from a target antigen and a suitable adjuvant. In another embodiment, the antibody is isolated from the serum of an animal such as a cow, horse, rabbit, or goat that has been immunized with an antigen and/or peptide derived from an antigen and a suitable adjuvant.

In one embodiment, the antibody is a polyclonal antibody derived from milk or colostrum. In one embodiment, the polyclonal antibody is derived from the milk or colostrum of a ruminant such as a cow, goat, sheep, camel or water buffalo. In another embodiment, the antibody is isolated from the milk or colostrum of a human. In a preferred embodiment, the polyclonal antibody is isolated from the milk or colostrum of a bovine, preferably an immunized cow. Bovine colostrum (early milk) is a preferred source of antibodies for this invention. In cows, antibody does not cross the placenta, and thus all passive immunity is transferred to the newborn calf through the milk. As a result, cows secrete a large bolus of antibody into the colostrum immediately after parturition and approximately 50% of the protein in colostrum is immunoglobulin. In the first 4 hours after birth, immunoglobulin concentrations of 50 mg/ml are typically found in the colostrum {Butler and Kehrli, 2005, Mucosal Immunology, 1763-1793}, dropping to 25-30 mg/ml 24 hours later {Ontsouka et al., 2003, J Dairy Sci, 86, 2005-11}. Colostrum and milk are a uniquely safe source of polyclonal antibody for oral delivery. There is already extensive human exposure to bovine immunoglobulin, as regular milk contains 1.5 g/L IgG.

In one aspect, the invention provides methods of treating a patient using the therapeutic compositions of the invention. The term "patient" as used herein refers to an animal. Preferably the animal is a mammal. More preferably the mammal is a human. A "patient" also refers to, for example, dogs, cats, horses, cows, pigs, guinea pigs, fish, birds and the like. Thus, the compositions and methods of the invention are equally suitable for veterinary treatments. In one embodiment of the invention, antibodies are used to treat diseases or disorders of companion animals, work animals or animals raised for food. In one embodiment of the invention, stabilized antibodies are used to provide passive immunity to newborn animals, preferably to cows, horses, sheep or swine.

The terms "treatment" "treat" and "treating" encompasses alleviation, cure or prevention of at least one symptom or other aspect of a disorder, disease, illness or other condition (collectively referred to herein as a "condition"), or reduction of severity of the condition, and the like. A composition of the invention need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. In one embodiment, an indication that a therapeutically effective amount of a composition has been administered to the patient is a sustained improvement over baseline of an indicator that reflects the severity of the particular disorder.

The pharmaceutical compositions of the present invention comprise a therapeutically effective amount of an antibody of the present invention formulated together with one or more pharmaceutically acceptable carriers or excipients. By a "therapeutically effective amount" of an antibody of the invention is meant an amount of the composition which confers a therapeutic effect on the treated subject, at a reasonable benefit/risk ratio applicable to any medical treatment. The therapeutic effect is sufficient to "treat" the patient as that term is used herein.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Compositions for rectal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound. In one embodiment, compositions for rectal administration are in the form of an enema.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Although stabilized antibodies have enhanced stability to gastric degradation, it may be desirable under some conditions to provide additional levels of protection against gastric degradation. If this is desired, there are many options for enteric coating (see for example U.S. Pat. Nos. 4,330,338 and 4,518,433). In one embodiment, enteric coatings take advantage of the post-gastric change in pH to dissolve a film coating and release the active ingredient. Coatings and formulations have been developed to deliver protein therapeutics to the small intestine and these approaches could be adapted for the delivery of an antibody of the invention. For example, an enteric-coated form of insulin has been developed for oral delivery {Toorisaka et al., 2005, J Control Release, 107, 91-6}.

In addition, the solid dosage forms of tablets, dragees, capsules, pills, and granules can be prepared with other coatings and shells well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Effective doses will vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the timing of delivery of the compound relative to food intake; the duration of the treatment; drugs used in combination or contemporaneously with the specific compound employed; and like factors well known in the medical arts.

Particular embodiments of the present invention involve administering a pharmaceutical composition comprising an antibody of the invention at a dosage of from about 1 mg per day to about 1 g/day, more preferably from about 10 mg/day to about 500 mg/day, and most preferably from about 20 mg/day to about 100 mg/day, to a subject. In one embodiment, a polyclonal antibody preparation is administered at a dosage of antibody from about 100 mg to about 50 g/day, more preferably from about 500 mg/day to about 10 g/day, and most preferably from about 1 g/day to about 5 g/day, to a subject, wherein the polyclonal antibody preparation has not been enriched for antibodies specific for the target antigen.

Treatment regimens include administering an antibody composition of the invention one time per day, two times per day, or three or more times per day, to treat a medical disorder disclosed herein. In one embodiment, an antibody composition of the invention is administered four times per day, 6 times per day or 8 times per day to treat a medical disorder disclosed herein. In one embodiment, an antibody composition of the invention is administered one time per week, two times per week, or three or more times per week, to treat a medical disorder disclosed herein.

The methods and compositions of the invention include the use of an antibody of the invention in combination with one or more additional therapeutic agents useful in treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which an antibody of the invention is administered at least once during a course of treatment that involves administering at least one other therapeutic agent to the patient.

The following examples are provided for the purpose of illustrating specific embodiments or features of the invention and are not intended to limit its scope.

EXAMPLES

Example 1

Treatment of Radiation-Induced Mucositis by Topical Application of Anti-TNF Antibody Mucositis was induced in Golden Syrian hamsters (male, 5-6 weeks old, 8 animals per group, Charles River Laboratories) using a standardized acute radiation protocol. A single dose of radiation (40 Gy/dose) was administered to all animals on day 0. Radiation was generated with a 160 kilovolt potential (15-ma) source at a focal distance of 50 cm, hardened with a 0.35 mm Cu filtration system. Irradiation targeted the left buccal pouch mucosa at a rate of 2.0 Gy/minute. Prior to irradiation, animals were anesthetized with an i.p. injection of Ketamine (160 mg/ml) and Xylazine (8 mg/ml). The left buccal pouch was everted, fixed and isolated using a lead shield.

Hamsters were administered purified rabbit anti-mouse TNF antibody (BioVision, Mountain View, Calif.) twice a day in the left buccal cheek pouch for 14 days starting on day −1 (day −1 to day 12). Antibody was administered in 0.2 ml, the approximate capacity of the cheek pouch. Two doses of antibody were compared (4.0 μg and 0.4 μg) and a vehicle saline control.

Mucositis was evaluated starting on day 6, and continuing on alternate days until day 28. Animals were anesthetized and the left cheek pouch everted and photographed. At the end of the study, the images were randomized and scored in an independent manner by 2 scorers who were blinded as to the identifiers for each image. The scale ranges from 0 for normal, to 5 for severe ulceration as is shown in the accompanying table. A score of 1-2 is considered to represent a mild stage of the disease, while a score of 3-5 is considered to represent moderate to severe mucositis. On day 28, all animals were sacrificed.

efficacy of antibody treatment under these conditions demonstrate that topically applied antibody accessed the area beneath the mucosal barrier, even prior to the formation of frank ulcers.

Example 2

Trafficking of Topically Applied Antibody in Irradiated Oral Mucosa

Mucositis is induced in Syrian Golden hamsters (male, 5-6 weeks old, 5 animals per group, Charles River Laboratories) using a standardized acute radiation protocol. A single dose of radiation (40 Gy/dose) is administered to all animals on day 0. Radiation is generated with a 160 kilovolt potential (15-ma) source at a focal distance of 50 cm, hardened with a 0.35 mm Cu filtration system. Irradiation targets the left buccal pouch mucosa at a rate of 2.0 Gy/minute. Prior to irradiation, animals are anesthetized with an i.p. injection of Ketamine (160 mg/ml) and Xylazine (8 mg/ml). The left buccal pouch is everted, fixed and isolated using a lead shield.

At varying times after radiation, anti-TNF antibody isolated from the colostrum of cows immunized with murine

| Score | Description |
|---|---|
| 0 | Pouch completely healthy. No erythema or vasodilation |
| 1 | Light to severe erythema and vasodilation. No erosion of mucosa |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray color due to pseudomembrane. Cumulative size of ulcers should equal about ¼ of the pouch. Severe erythema and vasodilation |
| 4 | Cumulative size of ulcers should equal about ½ of the pouch. Loss of pliability. Severe erythema and vasodilation |
| 5 | Virtually all of pouch is ulcerated. Loss of pliability (pouch can only partially be extracted from mouth |

The severity and duration of ulcerative mucositis was less severe in animals receiving the 4.0 μg dose of anti-TNF antibody than in the animals treated with saline vehicle control. Vehicle-treated animals exhibited a peak mucositis score of 3.6 on day 16 which had decreased to an average score of 2.1 by day 28. The group treated with the 4.0 μg dose of antibody had an average peak score of 3.3 on day 18 that decreased to 1.5 by day 28. The 0.4 μg/dose anti-TNF treatment failed to demonstrate any efficacy in the treatment of oral mucositis compared to the saline control.

The significance of the differences between the vehicle control and the treated groups was assessed by comparing the number of days with an ulcer (i.e. a score of 3 or higher) using a chi-squared ($\chi 2$) test. The vehicle control group had scores of 3 or higher on 58.3% of the animal days evaluated. The group treated with the low 0.4 μg/dose of anti-TNF had scores of 3 or higher on 56.8% of the days evaluated. The group treated with 4.0 μg/dose anti TNF antibody exhibited scores of 3 or higher on 46.4% of the days evaluated. The 11.9% reduction seen in the high dose group was highly significant when compared with the vehicle-treated group (p<0.025).

In this study, the final day of dosing with antibody was on day 12. At that time, only 5 of the 28 animals in the study had developed ulcers (grade 3 mucositis). In the high dose antibody group, only 1 animal had a score of 3 on day 12, and the majority of animals (5/8) had a score of less than 2. The TNF is applied to both the left and right cheek pouches and animals are sacrificed 1 hr later. Two time points are examined: day 6, when mucositis is beginning to develop, and day 14, when the severity of mucositis is at its peak.

The location of bovine antibody is tracked using polyclonal sheep anti-bovine IgG (h+l) antibody. Sections of the buccal mucosa are fixed in 10% buffered formalin and embedded in paraffin using standard techniques and longitudinal sections (5 μm thick) are cut. Slides are deparaffinated, rehydrated and treated with ExtrAvidin (Sigma-Aldrich) to inhibit endogenous biotin background. Slides are blocked with 1% gelatin in PBS and incubated with biotin labeled sheep anti-bovine IgG (h+l). After washing, the slides are treated with alkaline phosphatase-labeled ExtrAvidin, followed by BCIP/NBT as a substrate. The location of bovine immunoglobulin is determined microscopically. Slides are read by 2 individuals blinded as to the identity of the samples. Five slides are prepared and read from each cheek pouch and scored on a scale of 0-3 (0, no detectable antibody; 1, low level antibody staining; 2, moderate antibody staining; 3, intense antibody staining) Little or no antibody is detected in the control, non-irradiated cheek. Anti-TNF antibody is seen penetrating the buccal mucosa in the irradiated cheek pouch at days 6 and 14.

Example 3

Treatment of GI Mucositis in Chemotherapy-Induced Mucositis Model

GI mucositis in mice is induced by intraperitoneal administration of irinotecan hydrochloride (75 mg/kg) or saline to male Swiss mice (25-35 g) once per day for 4 consecutive days. Starting on day 1, mice are administered immunoglobulin purified from the colostrum of cows immunized with murine TNF; immunoglobulin is administered by oral gavage twice per day. Mice receive anti-TNF antibody or control anti-influenza antibody (20 mg per dose). The animals are evaluated daily through day 7 for the presence of diarrhea. Diarrhea observed after the final dose of irinotecan is considered to be delayed onset diarrhea. The severity of diarrhea is assessed using the following scale: 0-normal, normal stool or absent; 1-slight, slightly wet and soft stool; 2-moderate, wet and unformed stool with moderate perianal staining of the coat; and 3-severe, watery stool with severe perianal staining of the coat. Dosing with anti-TNF antibody, but not anti-influenza antibody reduces the incidence of severe delayed onset diarrhea.

Example 4

Treatment of Burn-Induced Intestinal Injury with Oral Anti-TNF Antibody

Severe burn induces intestinal injury and apoptosis of the intestinal epithelium. Male C57BL/6 mice (25-30 g, 5 mice per group) are anesthetized with methoxyflurane by inhalation and buprenorphine hydrochloride (0.1 mg/kg) by subcutaneous injection. The dorsum of the trunk is shaved and exposed to a steam burn in a 3×4 cm section of the back, resulting in a 30% surface area scald burn. Sham control animals are anesthetized, shaved and handled identically to the burned animals without exposure to steam. Animals are resuscitated with 0.9% NaCl-1 ml s.c. and 1 ml i.p. Immediately prior to administration of the burn (or sham burn), mice are administered a single dose of immunoglobulin by oral gavage. Immunoglobulin is purified from the colostrum of cows immunized with murine TNF or control anti-influenza antibody (20 mg per dose). Animals are sacrificed 12 hr after injury and the small intestine is excised, flushed with saline and weighed. A 2 cm section of the proximal small bowel is fixed in 10% formalin. Formalin fixed tissues are embedded in paraffin and three 3 μm sections are obtained at 40 μm intervals, deparaffinized, rehydrated and washed. H&E staining is performed and mucosal height, crypt depth and villus height is determined by measuring 10 randomly selected villi from each section. Injured animals are found to have reduced small bowel weight, reduced mucosal height and reduced villus height when compared to sham burned animals. Treatment with anti-TNF antibody, but not control anti-influenza antibody, minimizes these pathological burn-induced changes.

Example 5

Trafficking of Topically Applied Antibody in the Small Intestine in Mice Suffering Severe Burns Severe burn is known to induce intestinal injury and apoptosis of the intestinal epithelium. Male C57BL/6 mice (25-30 g, 5 mice per group) are anesthetized with methoxyflurane by inhalation and buprenorphine hydrochloride (0.1 mg/kg) by subcutaneous injection. The dorsum of the trunk is shaved and exposed to a steam burn in a 3×4 cm section of the back, resulting in a 30% surface area scald burn. Sham control animals are anesthetized, shaved and handled identically to the burned animals without exposure to steam. Animals are resuscitated with 0.9% NaCl-1 ml s.c. and 1 ml i.p. Immediately prior to administration of the burn (or sham burn), mice are administered a single dose of immunoglobulin by oral gavage. Immunoglobulin is purified from the colostrum of cows immunized with murine TNF or control anti-influenza antibody (20 mg per dose). Animals are sacrificed 12 hr after injury and the small intestine is excised and weighed. 3 cm sections from the proximal and distal small intestine are fixed in paraffin and sectioned. Slides are deparaffinated, rehydrated and treated with ExtrAvidin (Sigma-Aldrich) to inhibit endogenous biotin background. Slides are blocked with 1% gelatin in PBS and incubated with biotin labeled sheep anti-bovine IgG (h+1). After washing, the slides are treated with alkaline phosphatase-labeled ExtrAvidin, followed by BCIP/NBT as a substrate. The location of bovine immunoglobulin is determined microscopically. Five slides from each location will be prepared and read from each animal and scored on a scale of 0-3 (0, no detectable antibody; 1, low level antibody staining; 2, moderate antibody staining; 3, intense antibody staining. Anti-TNF antibody is detected below the mucosal barrier in burned mice, but not in sham-burned mice.

Example 6

Effect of Glycosylation on Stability of Bovine Immunoglobulin to Gastric Digestion The stability of bovine immunoglobulin to GI digestion is assessed in vitro.

Bovine immunoglobulin is purified from colostrum. Bovine colostrums are collected from 6 cows on days 1-4 after parturition, pooled and frozen at −20° C. until further use. Colostrum is thawed and centrifuged at 4000×g to remove fat. The pH is adjusted to 4.6 using 1 N HCl, incubated for 30 min at 37° C. to precipitate casein, and centrifuged. The pH is raised to 7.2 and the whey is stored at −20° C. Immunoglobulin is purified by precipitation with 50% (vol/vol) saturated ammonium sulfate and ammonium sulfate is removed by diafiltration. The Ig-enriched colostral whey is fractionated on a column of immobilized jacalin (Pierce, Rockford, Ill.); jacalin is a lectin that recognizes an O-linked glycan present on human IgA and a subset of bovine IgG. The immunoglobulin solution (10 mg/ml) is loaded onto the column and washed with PBS. The flow-through material (jacalin-non-binding) is collected and the column is extensively washed. Bound material is eluted with 0.4 M D-galactose (jacalin-binding) and dialyzed against PBS.

To mimic transit through the stomach, purified IgG is incubated for varying times with pepsin, pH 2.0 at 37° C. IgG is buffer exchanged into 0.2 M acetate, pH 2.0. Five ml samples at 1.5 mg/ml are incubated at 37° C. with or without 0.05 mg/ml pepsin (Sigma-Aldrich, St. Louis, Mo.). One ml aliquots are removed at varying times (1, 2, 4, 6 hr), and the pH raised by adding 200 μl Tris base. Samples are dialyzed into PBS and stored at 4° C. with 0.02% $NaN_3$. Samples are analyzed by SDS-PAGE to determine the degree of immunoglobulin fragmentation. Jacalin-binding immunoglobulin is found to be more stable to digestion than is jacalin-non-binding immunoglobulin.

Example 7

Effect of Glycosylation on Stability of Bovine Immunoglobulin to Digestion with Bacterial Proteases of the Oral Cavity Bovine immunoglobulin is purified from colostrum. Bovine colostrums are collected from 6 cows on days 1-4 after parturition, pooled and frozen at −20° C. until further use. Colostrum is thawed and centrifuged at 4000×g to remove fat. The pH is adjusted to 4.6 using 1 N HCl, incubated for 30 min at 37° C. to precipitate casein, and centrifuged. The pH is raised to 7.2 and the whey is stored at −20° C. Immunoglobulin is purified by precipitation with 50% (vol/vol) saturated ammonium sulfate and ammonium sulfate is removed by diafiltration. The Ig-enriched colostral whey is fractionated on a column of immobilized jacalin (Pierce, Rockford, Ill.); jacalin is a lectin that recognizes an O-linked glycan present on human IgA and a subset of bovine IgG. The immunoglobulin solution (10 mg/ml) is loaded onto the column and washed with PBS. The flow-through material (jacalin-non-binding) is collected and the columns are extensively washed. Bound material is eluted with 0.4 M D-galactose and dialyzed against PBS (jacalin-binding).

Bacterial strains isolated from the oral cavity are obtained from American Type Culture Collection (Rockville, Md.). Ten strains are examined: *Capnocytophaga ochracea* (ATCC#27872), *Streptococcus mutans* (ATCC#700611), *Streptococcus intermedius* (ATCC#31412), *Prevotella intermedia* (ATCC#15032), *Prevotella intermedia* (ATCC#15033), *Prevotella nigrescens* (ATCC#25261), *Prevotella loescheii* (ATCC#15930), *Prophyromanas catoniae* (ATCC#51270), *Treponema denticola* (ATCC#700771) and *Lactobacillus plantarum* (ATCC#BAA-793). All strains are cultivated under the conditions recommended by ATCC. Individual colonies from 3- to 4-day plate cultures are suspended in 40 μl of a 5 mg/ml solution of purified immunoglobulin in 0.85% NaCl 0.05 M Tris-HCl, pH 7.4. Purified human IgG and IgA (SigmaAldrich) are used as controls. After 18 hr incubation at 35° C., samples are analyzed by SDS-PAGE under reducing conditions. Some bacterial strains are found to express proteases that degrade human IgA and IgG. At least some proteases are found to have less activity against bovine immunoglobulin than against human immunoglobulin. At least some proteases are found to have less activity against jacalin-binding bovine immunoglobulin than against jacalin-non-binding bovine immunoglobulin.

Example 8

Variability of Glycosylation in Bovine Colostral Immunoglobulin

Colostrum is collected on the day following calving from 12 immunized cows (six cows are immunized with murine TNF and six are immunized with gliadin) and frozen at −20° C. until further use. Samples from each cow are handled separately. Colostrum is thawed and centrifuged at 4000×g to remove fat. The pH is adjusted to 4.6 using 1 N HCl, incubated for 30 min at 37° C. to precipitate casein, and centrifuged. The pH is raised to 7.2 and the whey is stored at −20° C. Immunoglobulin is purified by precipitation with 50% (vol/vol) saturated ammonium sulfate and ammonium sulfate is removed by diafiltration. Samples from each colostrum sample are separated on SDS-PAGE and Western blotted with biotinylated jacalin (Vector Laboratories, Burlingame, Calif.). Colostrum samples from different animals are found to display different levels of jacalin binding.

Example 9

Effect of Pregnancy on Antibody Glycosylation

A serum sample is collected from a pregnant cow within one week of the expected parturition date and a second sample is collected approximately one day after calving. Serum samples are also collected from a never-pregnant female cow and an age-matched steer. Glycosylation of antibodies is detected by ELISA. ELISA plates are coated with rabbit anti-bovine (IgG+IgA+IgM) antibody (Bethyl Laboratories, Montgomery, Tex.) and washed. Two-fold serial dilutions of each serum sample are applied to the microtiter plates in triplicate wells and washed again. Plates are developed using biotin-labeled jacalin (Vector Laboratories, Burlingame, Calif.) followed by HRP-labeled streptavidin and OPD. Serum immunoglobulin from a cow near the time of birth is found to display a different level of jacalin binding than is immunoglobulin from a male or never-pregnant female cow.

Example 10

Measurement of Glycosylation of Bovine Immunoglobulin for Process Development and Release Testing Fifty cows are immunized with gliadin to generate antibody to be used in the treatment of celiac disease. Day one colostrum samples from each cow are assayed for jacalin binding as a measure of O-glycosylation. Colostral whey is prepared from each sample and assayed by ELISA on plates coated with rabbit anti-bovine IgG1 and developed with biotinylated jacalin and HRP-streptavidin. Colostrum samples that have glycosylation levels that fall within pre-defined specifications are accepted and used for manufacture of the commercial antibody product. Colostrum samples that fall outside of the pre-defined specifications are rejected and the colostrum is discarded.

Example 11

Effect of Glycosylation on Ability of Antibody to Penetrate Damaged Mucosal Membranes Anti-TNF antibody is isolated from the colostrum of cows immunized with murine TNF. The antibody is fractionated and processed to generate separate preparations with defined patterns of glycosylation. Four preparations are compared: 1) jacalin-non-binding antibody, prepared by passing the antibody over a jacalin-agarose column; 2) jacalin-binding antibody, prepared by binding the antibody to a jacalin-agarose column and eluting the antibody with 0.4 M D-galactose; 3) a glycoform of antibody in which sialic acid and terminal β-galactose residues are removed by incubation of antibody (100 mg in 10.0 ml in 100 mM MES buffer, H 7.0) with sialidase A (*A. ureafaciens*, 100 milliunits) and β-galactosidase (*D. pneumoniae*, 100 milliunits) for 24 hr at 37° C.; 4) a glycoform of antibody which is maximally sialylated by incubation of antibody (100 mg in 10.0 ml in 100 mM MES buffer, pH 7.0) with 50 milliunits each of β1,4-galactosyltransferase and α-2,3-sialyltransferase and 5 umol each of UDP-galactose, CMP-N-acetylneuraminic acid and $MnCl_2$ for 24 hr at 37° C.

Mucositis is induced in Syrian Golden hamsters (male, 5-6 weeks old, 5 animals per group, Charles River Laboratories) using a standardized acute radiation protocol. A single dose of radiation (40 Gy/dose) is administered to all animals on day 0. Radiation is generated with a 160 kilovolt potential (15-ma) source at a focal distance of 50 cm, hardened with a 0.35 mm Cu filtration system. Irradiation targets the left buccal pouch mucosa at a rate of 2.0 Gy/minute. Prior to irradiation, animals are anesthetized with an i.p. injection of Ketamine (160 mg/ml) and Xylazine (8 mg/ml). The left buccal pouch is everted, fixed and isolated using a lead shield.

After 8 days, when the buccal membrane is partially permeabilized, antibody is applied to both the left and right cheek pouches and animals are sacrificed 1 hr later. The location of bovine antibody is tracked using polyclonal sheep anti-bovine IgG (h+l) antibody. Sections of the buccal mucosa are fixed in 10% buffered formalin and embedded in paraffin using standard techniques and longitudinal sections (5 μm thick) are cut. Slides are deparaffinated, rehydrated and treated with ExtrAvidin (Sigma-Aldrich) to inhibit endogenous biotin background. Slides are blocked with 1% gelatin in PBS and incubated with biotin labeled sheep anti-bovine IgG (h+l). After washing, the slides are treated with alkaline phosphatase-labeled ExtrAvidin, followed by BCIP/NBT as a substrate. The location of bovine immunoglobulin is determined microscopically. Slides are read by 2 individuals blinded as to the identity of the samples. Five slides are prepared and read from each cheek pouch and scored on a scale of 0-3 (0, no detectable antibody; 1, low level antibody staining; 2, moderate antibody staining; 3, intense antibody staining). The extent of antibody crossing the damaged mucosal membrane is found to be dependent on the glycosylation state of the antibody.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:

1. A composition for oral delivery to a human patient comprising polyclonal antibodies specific to TNF, wherein the antibodies are obtained from the milk or colostrum of a ruminant that has been immunized with TNF or any antigenic fragment thereof, and wherein upon oral administration to the digestive tract of the patient, the composition is therapeutically effective to treat inflammatory bowel disease in the patient, and wherein the antibodies specific to TNF are present in the composition at a dosage of about 1 mg per day to about 1 gram per day.

2. The composition of claim 1 formulated as a solid dosage form for oral administration.

3. The composition of claim 2 wherein the solid dosage form is selected from capsules, tablets, pills powders and granules.

4. The composition of claim 2 wherein the solid dosage form comprises an enteric coating.

5. The composition of claim 1 wherein the ruminant is a bovine.

6. A method of treating inflammatory bowel disease in a human patient in need thereof comprising orally administering to a patient, a composition of claim 1.

* * * * *